US011471280B2

(12) United States Patent
Adams

(10) Patent No.: US 11,471,280 B2
(45) Date of Patent: *Oct. 18, 2022

(54) ASYMMETRIC MITRAL ANNULOPLASTY BAND

(71) Applicant: Edwards Lifesciences LLC, Irvine, CA (US)

(72) Inventor: David H. Adams, New York, NY (US)

(73) Assignee: Edwards Lifesciences, LLC, Irvine, CA (US)

(*) Notice: Subject to any disclaimer, the term of this patent is extended or adjusted under 35 U.S.C. 154(b) by 377 days.

This patent is subject to a terminal disclaimer.

(21) Appl. No.: 16/434,961

(22) Filed: Jun. 7, 2019

(65) Prior Publication Data

US 2019/0290430 A1 Sep. 26, 2019

Related U.S. Application Data

(63) Continuation of application No. 15/177,112, filed on Jun. 8, 2016, now Pat. No. 10,314,707.

(Continued)

(51) Int. Cl.
*A61F 2/24* (2006.01)

(52) U.S. Cl.
CPC .............. *A61F 2/2445* (2013.01); *A61F 2/24* (2013.01); *A61F 2/2442* (2013.01);
(Continued)

(58) Field of Classification Search
CPC ........ A61F 2/24; A61F 2/2442; A61F 2/2445; A61F 2/2448; A61F 2230/0034
See application file for complete search history.

(56) References Cited

U.S. PATENT DOCUMENTS

| 3,656,185 A | 4/1972 | Carpentier |
| 4,055,861 A | 11/1977 | Carpentier et al. |

(Continued)

FOREIGN PATENT DOCUMENTS

| CN | 103153231 A | 6/2013 |
| EP | 0338994 A1 | 10/1989 |

(Continued)

OTHER PUBLICATIONS

Adams, David, et al., "Large Annuloplasty Rings Facilitate Mitral Valve Repair in Barlow's Disease," Society of Thoracic Surgeons 42.sup.nd Annual Meeting, Jan. 30-Feb. 1, 2006.

(Continued)

*Primary Examiner* — Seema Mathew
(74) *Attorney, Agent, or Firm* — Guy Cumberbatch

(57) ABSTRACT

An annuloplasty band and method of implantation. The band is shaped and sized to avoid the adjacent aortic valve structure and better protects against dehiscence along the muscular mitral annulus. The band is asymmetric and when implanted spans more around the side of the mitral annulus having the posterior commissure than the side with the anterior commissure. The band has a saddle shape with a posterior upward bow centered on a minor axis of the mitral annulus, and a span extending clockwise therefrom is longer than a span extending counter-clockwise. A set of rings may have different saddle profiles and different plan view shapes for different sized bands. A method includes implanting so that the band extends over the posterior leaflet and a short distance past the posterior commissure outside of the anterior leaflet.

20 Claims, 4 Drawing Sheets

Related U.S. Application Data

(60) Provisional application No. 62/173,294, filed on Jun. 9, 2015.

(52) U.S. Cl.
CPC .... *A61F 2/2448* (2013.01); *A61F 2230/0015* (2013.01); *A61F 2230/0034* (2013.01); *A61F 2230/0095* (2013.01)

(56) References Cited

U.S. PATENT DOCUMENTS

| | | |
|---|---|---|
| 4,164,046 A | 8/1979 | Cooley |
| 4,217,665 A | 8/1980 | Bex et al. |
| 4,275,469 A | 6/1981 | Gabbay |
| 4,602,911 A | 7/1986 | Ahmadi et al. |
| 4,790,844 A | 12/1988 | Ovil |
| 4,917,097 A | 4/1990 | Proudian et al. |
| 4,993,428 A | 2/1991 | Arms |
| 5,010,892 A | 4/1991 | Colvin et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,316,016 A | 5/1994 | Adams et al. |
| 5,344,442 A | 9/1994 | Deac |
| 5,396,887 A | 3/1995 | Imran |
| 5,397,348 A | 3/1995 | Campbell et al. |
| 5,450,860 A | 9/1995 | O'Connor |
| 5,480,424 A | 1/1996 | Cox |
| 5,496,336 A | 3/1996 | Cosgrove et al. |
| 5,533,515 A | 7/1996 | Coller et al. |
| 5,573,007 A | 11/1996 | Bobo, Sr. |
| 5,593,435 A | 1/1997 | Carpentier et al. |
| 5,607,471 A | 3/1997 | Seguin et al. |
| 5,662,704 A | 9/1997 | Gross |
| 5,674,279 A | 10/1997 | Wright et al. |
| 5,728,064 A | 3/1998 | Burns et al. |
| 5,733,331 A | 3/1998 | Peredo |
| 5,752,522 A | 5/1998 | Murphy |
| 5,776,189 A | 7/1998 | Khalid |
| 5,814,098 A | 9/1998 | Hinnenkamp et al. |
| 5,824,066 A | 10/1998 | Gross |
| 5,824,069 A | 10/1998 | Lemole |
| 5,848,969 A | 12/1998 | Panescu et al. |
| 5,855,563 A | 1/1999 | Kaplan et al. |
| 5,865,801 A | 2/1999 | Houser |
| 5,888,240 A | 3/1999 | Carpentier et al. |
| 5,902,308 A | 5/1999 | Murphy |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,931,868 A | 8/1999 | Gross |
| 5,972,030 A | 10/1999 | Garrison et al. |
| 6,001,127 A | 12/1999 | Schoon et al. |
| 6,010,531 A | 1/2000 | Donlon et al. |
| 6,019,739 A | 2/2000 | Rhee et al. |
| 6,024,918 A | 2/2000 | Hendriks et al. |
| 6,042,554 A | 3/2000 | Rosenman et al. |
| 6,066,160 A | 5/2000 | Colvin et al. |
| 6,081,737 A | 6/2000 | Shah |
| 6,083,179 A | 7/2000 | Oredsson |
| 6,099,475 A | 8/2000 | Seward et al. |
| 6,102,945 A * | 8/2000 | Campbell ............. A61F 2/2448 623/2.37 |
| 6,110,200 A | 8/2000 | Hinnenkamp |
| 6,117,091 A | 9/2000 | Young et al. |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,312,464 B1 | 11/2001 | Navia |
| 6,332,893 B1 | 12/2001 | Mortier et al. |
| 6,368,348 B1 | 4/2002 | Gabbay |
| 6,391,054 B2 | 5/2002 | Carpentier et al. |
| 6,406,420 B1 | 6/2002 | McCarthy et al. |
| 6,406,493 B1 | 6/2002 | Tu et al. |
| 6,409,759 B1 | 6/2002 | Peredo |
| 6,419,696 B1 | 7/2002 | Ortiz et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,723,038 B1 | 4/2004 | Schroeder et al. |
| 6,726,715 B2 | 4/2004 | Sutherland |
| 6,726,717 B2 | 4/2004 | Alfieri et al. |
| 6,749,630 B2 | 6/2004 | McCarthy et al. |
| 6,764,510 B2 | 7/2004 | Vidlund et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,830,586 B2 | 12/2004 | Quijano et al. |
| 6,858,039 B2 | 2/2005 | McCarthy |
| 6,908,482 B2 | 6/2005 | McCarthy et al. |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,945,996 B2 | 9/2005 | Sedransk |
| 6,955,689 B2 | 10/2005 | Ryan et al. |
| 6,966,924 B2 | 11/2005 | Holmberg |
| 6,977,950 B1 | 12/2005 | Krishnamoorthy |
| 6,986,775 B2 | 1/2006 | Morales et al. |
| 7,037,334 B1 | 5/2006 | Hlavka et al. |
| 7,066,954 B2 | 6/2006 | Ryan et al. |
| 7,101,395 B2 | 9/2006 | Tremulis et al. |
| 7,112,219 B2 | 9/2006 | Vidlund et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,247,134 B2 | 7/2007 | Vidlund et al. |
| 7,294,148 B2 | 11/2007 | McCarthy |
| 7,329,280 B2 | 2/2008 | Bolling et al. |
| 7,361,190 B2 | 4/2008 | Shaoulian et al. |
| 7,527,647 B2 | 5/2009 | Spence |
| 7,608,103 B2 * | 10/2009 | McCarthy ............. A61F 2/2445 623/2.37 |
| 7,959,673 B2 | 6/2011 | Carpentier et al. |
| 7,988,725 B2 | 8/2011 | Gross et al. |
| 7,993,395 B2 | 8/2011 | Vanermen et al. |
| 8,123,802 B2 | 2/2012 | Kron et al. |
| 8,163,012 B2 * | 4/2012 | Fawzy .................. A61F 2/2448 623/2.37 |
| 8,216,303 B2 | 7/2012 | Navia |
| 8,241,351 B2 | 8/2012 | Cabiri |
| 8,277,502 B2 | 10/2012 | Miller et al. |
| 8,353,956 B2 | 1/2013 | Miller et al. |
| 8,460,173 B2 | 6/2013 | Schweich, Jr. et al. |
| 8,529,620 B2 | 9/2013 | Alfieri |
| 8,535,374 B2 | 9/2013 | Redmond et al. |
| 8,591,576 B2 | 11/2013 | Hasenkam et al. |
| 8,734,507 B2 | 5/2014 | Keranen |
| 8,764,821 B2 | 7/2014 | Carpentier et al. |
| 8,784,483 B2 | 7/2014 | Navia |
| 8,858,623 B2 | 10/2014 | Miller et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 9,192,472 B2 | 11/2015 | Gross et al. |
| 9,326,858 B2 | 5/2016 | Migliazza et al. |
| 9,339,381 B2 * | 5/2016 | Johnson ................ A61F 2/2418 |
| 9,414,922 B2 | 8/2016 | McCarthy et al. |

(56) References Cited

U.S. PATENT DOCUMENTS

| | | | |
|---|---|---|---|
| 9,526,613 B2 | 12/2016 | Gross et al. | |
| 9,610,162 B2 | 4/2017 | Zipory et al. | |
| 9,662,209 B2 | 5/2017 | Gross et al. | |
| 9,937,041 B2* | 4/2018 | Carpentier | A61F 2/2448 |
| 10,166,101 B2 | 1/2019 | Alfieri et al. | |
| 2001/0034551 A1 | 10/2001 | Cox | |
| 2002/0129820 A1 | 9/2002 | Ryan et al. | |
| 2002/0133180 A1 | 9/2002 | Ryan et al. | |
| 2002/0169504 A1 | 11/2002 | Alferness et al. | |
| 2002/0173844 A1 | 11/2002 | Alfieri et al. | |
| 2003/0033009 A1 | 2/2003 | Gabbay | |
| 2003/0040793 A1 | 2/2003 | Marquez | |
| 2003/0045929 A1 | 3/2003 | McCarthy et al. | |
| 2003/0078653 A1 | 4/2003 | Vesely et al. | |
| 2003/0083742 A1 | 5/2003 | Spence et al. | |
| 2003/0093148 A1* | 5/2003 | Bolling | A61F 2/2448 623/2.36 |
| 2003/0105519 A1 | 6/2003 | Fasol et al. | |
| 2004/0006384 A1 | 1/2004 | McCarthy | |
| 2004/0088047 A1 | 5/2004 | Spence et al. | |
| 2004/0122513 A1 | 6/2004 | Navia et al. | |
| 2004/0186566 A1 | 9/2004 | Hindrichs et al. | |
| 2004/0249452 A1* | 12/2004 | Adams | A61F 2/2451 623/2.36 |
| 2004/0249453 A1 | 12/2004 | Cartledge et al. | |
| 2005/0004665 A1* | 1/2005 | Aklog | A61F 2/2448 623/2.36 |
| 2005/0004666 A1 | 1/2005 | Alfieri et al. | |
| 2005/0043791 A1 | 2/2005 | McCarthy et al. | |
| 2005/0070999 A1 | 3/2005 | Spence | |
| 2005/0075727 A1 | 4/2005 | Wheatley | |
| 2005/0131533 A1 | 6/2005 | Alfieri et al. | |
| 2005/0182487 A1 | 8/2005 | McCarthy et al. | |
| 2005/0192666 A1* | 9/2005 | McCarthy | A61F 2/2445 623/2.36 |
| 2005/0197696 A1 | 9/2005 | Gomez Duran | |
| 2005/0246014 A1* | 11/2005 | McCarthy | A61F 2/2448 623/2.36 |
| 2005/0256567 A1 | 11/2005 | Lim et al. | |
| 2005/0256568 A1* | 11/2005 | Lim | A61F 2/2448 623/2.36 |
| 2005/0256569 A1 | 11/2005 | Lim et al. | |
| 2005/0267572 A1 | 12/2005 | Schoon et al. | |
| 2005/0278022 A1 | 12/2005 | Lim | |
| 2005/0288776 A1 | 12/2005 | Shaoulian et al. | |
| 2005/0288777 A1 | 12/2005 | Rhee et al. | |
| 2005/0288778 A1 | 12/2005 | Shaoulian et al. | |
| 2005/0288780 A1 | 12/2005 | Rhee et al. | |
| 2005/0288782 A1 | 12/2005 | Moaddeb et al. | |
| 2005/0288783 A1 | 12/2005 | Shaoulian et al. | |
| 2006/0015178 A1 | 1/2006 | Moaddeb et al. | |
| 2006/0015179 A1 | 1/2006 | Bulman-Fleming et al. | |
| 2006/0020336 A1 | 1/2006 | Liddicoat | |
| 2006/0025856 A1 | 2/2006 | Ryan et al. | |
| 2006/0025858 A1 | 2/2006 | Alameddine | |
| 2006/0030885 A1 | 2/2006 | Hyde | |
| 2006/0129236 A1* | 6/2006 | McCarthy | A61F 2/2445 623/2.36 |
| 2006/0149368 A1 | 7/2006 | Spence | |
| 2006/0195183 A1 | 8/2006 | Navia et al. | |
| 2006/0217803 A1* | 9/2006 | Ingle | A61F 2/2448 623/2.11 |
| 2006/0259135 A1 | 11/2006 | Navia et al. | |
| 2007/0038294 A1 | 2/2007 | Navia | |
| 2007/0049952 A1 | 3/2007 | Weiss | |
| 2007/0050020 A1 | 3/2007 | Spence | |
| 2007/0066863 A1 | 3/2007 | Rafiee et al. | |
| 2007/0100439 A1 | 5/2007 | Cangialosi et al. | |
| 2007/0118151 A1 | 5/2007 | Davidson | |
| 2007/0123979 A1 | 5/2007 | Perier et al. | |
| 2007/0156234 A1* | 7/2007 | Adzich | A61F 2/2466 623/2.11 |
| 2007/0162111 A1 | 7/2007 | Fukamachi et al. | |
| 2007/0173930 A1 | 7/2007 | Sogard et al. | |
| 2007/0213582 A1 | 9/2007 | Zollinger et al. | |
| 2007/0255396 A1 | 11/2007 | Douk et al. | |
| 2008/0058924 A1* | 3/2008 | Ingle | A61F 2/2448 623/2.41 |
| 2008/0071365 A1 | 3/2008 | Ley | |
| 2008/0086203 A1 | 4/2008 | Roberts | |
| 2008/0275551 A1* | 11/2008 | Alfieri | A61F 2/2445 623/2.36 |
| 2009/0036979 A1 | 2/2009 | Redmond et al. | |
| 2009/0043381 A1 | 2/2009 | Macoviak et al. | |
| 2009/0177276 A1 | 7/2009 | Carpentier et al. | |
| 2009/0177278 A1 | 7/2009 | Spence | |
| 2009/0192602 A1 | 7/2009 | Kuehn | |
| 2009/0192603 A1 | 7/2009 | Kuehn | |
| 2009/0192604 A1 | 7/2009 | Gloss | |
| 2009/0192605 A1 | 7/2009 | Gloss et al. | |
| 2009/0192606 A1 | 7/2009 | Gloss et al. | |
| 2009/0287303 A1* | 11/2009 | Carpentier | A61F 2/2448 623/2.36 |
| 2010/0076549 A1* | 3/2010 | Keidar | A61F 2/2466 623/2.36 |
| 2010/0324670 A1* | 12/2010 | Kron | A61F 2/2448 623/2.36 |
| 2011/0093065 A1* | 4/2011 | Roberts | A61F 2/2445 623/2.37 |
| 2011/0160849 A1* | 6/2011 | Carpentier | A61F 2/2445 623/2.19 |
| 2012/0053687 A1* | 3/2012 | Migliazza | A61F 2/2445 623/2.37 |
| 2012/0071970 A1 | 3/2012 | Carpentier et al. | |
| 2012/0136435 A1* | 5/2012 | Brunnett | A61F 2/2442 623/2.36 |
| 2013/0204361 A1 | 8/2013 | Adams et al. | |
| 2014/0277420 A1* | 9/2014 | Migliazza | A61F 2/2445 29/428 |
| 2015/0265403 A1 | 9/2015 | Keranen | |
| 2016/0338830 A1 | 11/2016 | Jin et al. | |
| 2020/0146854 A1* | 5/2020 | Sirhan | A61F 2/915 |

FOREIGN PATENT DOCUMENTS

| | | |
|---|---|---|
| EP | 0860151 A1 | 8/1998 |
| EP | 1034753 A1 | 9/2000 |
| WO | 9742871 A1 | 11/1997 |
| WO | 0023007 A1 | 4/2000 |
| WO | 0187191 A1 | 11/2001 |
| WO | 2005004753 A1 | 1/2005 |
| WO | 2005034813 A2 | 4/2005 |
| WO | 2005122964 A1 | 12/2005 |
| WO | 2008063537 A2 | 5/2008 |
| WO | 2009139776 A1 | 11/2009 |
| WO | 2015013861 A1 | 2/2015 |

OTHER PUBLICATIONS

Alonso-Lei, Md., et al., Adjustable Annuloplasty for Tricuspid Insufficiency, The annals of Thoracic Surgery, vol. 46, No. 3, pp. 368-369, Sep. 1988.

Bolling, Mitral Valve Reconstruction in the Patient With Heart Failure, Heart Failure Reviews, 6, pp. 177-185, 2001.

Bolling, et al., Surgical Alternatives for Heart Failure, The Journal of Heart and Lung Transplantation, vol. 20, No. 7, pp. 729-733, 2001.

Caleya, et al., Fracture of Carpentier's Ring in a Patient with Tricuspid Annuloplasty Thoracic Cardiovascular Surgeon. vol. 31. pp. 175-176. 1983.

Carpentier, et al. "The 'Physio-Ring': An Advanced Concept in Mitral Valve Annuloplasty," Society of Thoracic Surgeons 31.sup.st Annual meeting, Jan. 30-Feb. 2, 1995.

Carpentier—Edwards Classic Annuloplasty Ring With Duraflo Treatment Models 4425 and 4525 for Mitral and Tricuspid Valvuloplsty, Baxter Healthcare Corporation, 1998.

Carpentier, et al., Reconstructive Valve Surgery, Chapters 17-19, ISBN No. 978-0-7216-9168-8, Sanders Elsevier Publishing, Maryland Heights, Missouri, 2010.

(56) References Cited

OTHER PUBLICATIONS

Carpentier—Edwards Physio Annuloplasty Ring, Edwards Lifesciences Corporation, 2003.

Cochran, et al., Effect of Papillary Muscle Position on Mitral Valve Function: Relationship to Homografts, The Society of Thoracic Surgeons, pp. 5155-5161, 1998.

Cosgrove—Edwards, Annuloplasty System. Edwards Lifesciences Corporation. 2000.

Cosgrove, et al., Initial Experience with the Cosgrove-Edwards Annuloplasty System. The Annals of Thoracic Surgery vol. 60. pp. 499-504. 1995.

D.C. Miller, IMR Redux—To Repair or Replace?, Journal of Thoracic & Cardiovascular Surgery, pp. 1-8,2001.

Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0694-7317/2000.

Galinanes, et al., Fracture of the Carpentier-Edwards Ring in Tricuspid Position: A Report of Three Cases. The Annals of Thoracic Surgery. vol. 42. pp. 74-76. 1986.

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261,2003.

Melo, et al., Atrioventricular Valve Repair Using Externally Adjustable Flexible Rings: The Journal of Thoracic Cardiovascular Surgery, vol. 110, No. 5, 1995.

MGH Study Shows Mitral Valve Prolapse Not a Stroke Risk Factor, Massachusetts General Hospital, pp. 1-3, Jun. 1999.

Navia, Jose Luis., Minimally Invasive Mitral Valve Surgery. Department of Thoracic and Cardiovascular Surgery, The Cleveland Clinic Foundation. 2001.

Salgo, et al., Effect of Annular Shape on Leaflet Curvature in Reducing Mitral Leaflet, American Heart Association, Circulation 200; pp. 106-711.

Seguin, et al., Advance in Mitral Valve Repair Using a Device Flexible in Three Dimensions, The St. Jude Medical—Seguin Annuloplasty Ring, ASAIO Journal, vol. 42, No. 6, pp. 368-371, 1996.

Smolens, et al., Mitral Valve Repair in Heart Failure, The European Journal of Heart Failure 2, pp. 365-371,2000.

Natanbe, Nozomi, et al. "Mitral Annulus Flattens in Ischemic Mitral Regurgitation: Geometric Differences Between Inferior and Anterior Myocardial Infarction: A Real-Time 3-Dimensional Echocardiographic Study," American Heart Association .COPVRGT. 2005; ISSN: 1524-4539.

Daimon, Md., et al., "Mitral Valve Repair With Carpentier-McCarthy-Adams IMR ETlogix Annuloplasty Ring for Ischemic Mitral Regurgitation", Cleveland Clinic Foundation, pp. I-588-I-593, Jul. 4, 2006.

\* cited by examiner

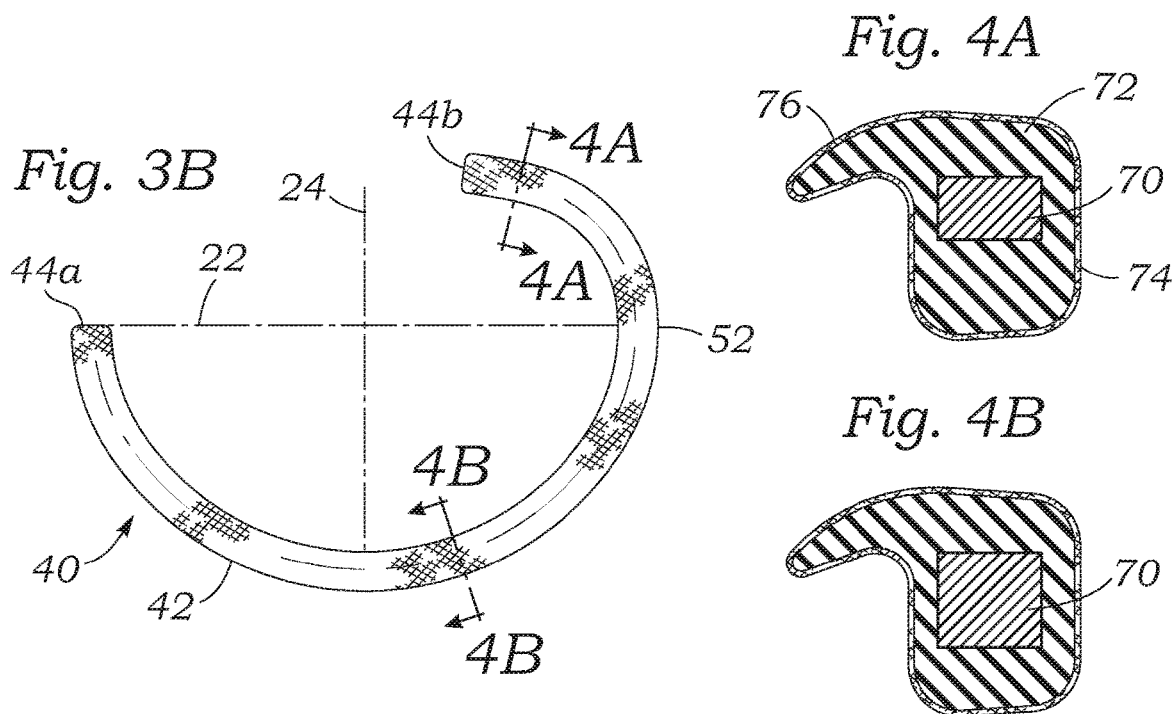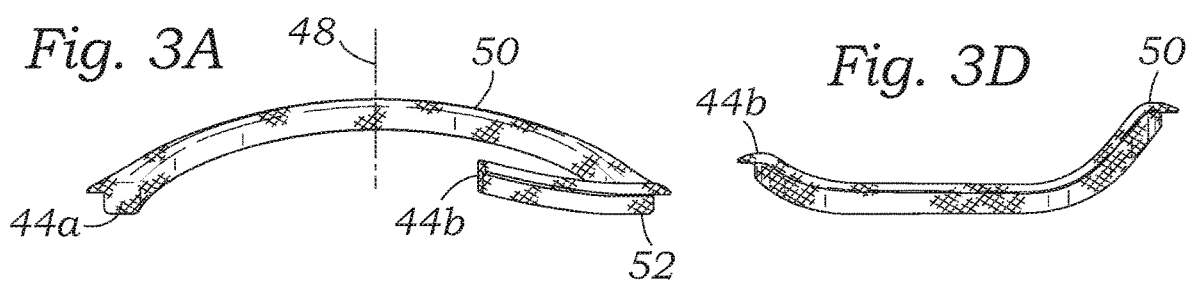

ASYMMETRIC MITRAL ANNULOPLASTY BAND

RELATED APPLICATIONS

The present application is a continuation of U.S. Ser. No. 15/177,112, filed Jun. 8, 2016, now U.S. Pat. No. 10,314,707, which claims priority to U.S. Provisional Ser. No. 62/173,294, filed Jun. 9, 2015, the contents of which are expressly incorporated herein.

TECHNICAL FIELD

The present invention relates generally to annuloplasty bands, and particularly to a mitral annuloplasty band.

BACKGROUND

In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice. The four valves ensure that blood does not flow in the wrong direction during the cardiac cycle; that is, to ensure that the blood does not back flow through the valve. Blood flows from the venous system and right atrium through the tricuspid valve to the right ventricle, then from the right ventricle through the pulmonary valve to the pulmonary artery and the lungs. Oxygenated blood then flows through the mitral valve from the left atrium to the left ventricle, and finally from the left ventricle through the aortic valve to the aorta/arterial system.

The mitral and tricuspid valves are defined by fibrous rings of collagen, each called an annulus, which forms a part of the fibrous skeleton of the heart. The annulus provides peripheral attachments for the two cusps or leaflets of the mitral valve (called the anterior and posterior cusps) and the three cusps or leaflets of the tricuspid valve. The native valve leaflets flex outward when the valve opens and their free edges come together or coapt in closure.

The free edges of the mitral leaflets connect to chordae tendineae from more than one papillary muscle. Mitral valve malfunction can result from the chordae tendineae (the chords) becoming stretched, and in some cases tearing. Also, a normally structured valve may not function properly because of an enlargement of or shape change in the valve annulus. This condition is referred to as a dilation of the annulus and generally results from heart muscle failure. In addition, the valve may be defective at birth or because of an acquired disease. From a number of etiologies, mitral valve dysfunction can occur when the leaflets do not coapt at peak contraction pressures. As a result, an undesired back flow of blood from the left ventricle into the left atrium can occur.

Various surgical techniques may be used to repair a diseased or damaged valve. A commonly used repair technique effective in treating incompetence is annuloplasty, which often involves reshaping the annulus by attaching a prosthetic annuloplasty repair segment or ring thereto. For instance, the goal of a posterior mitral annulus repair is to bring the posterior mitral leaflet forward toward to the anterior leaflet to better allow coaptation. The annuloplasty ring is designed to support the functional changes that occur during the cardiac cycle: maintaining coaptation and valve integrity to prevent reverse flow while permitting good hemodynamics during forward flow.

The annuloplasty ring typically comprises an inner substrate or core of a metal such as a rod or multiple bands of stainless steel or titanium, or a flexible material such as silicone rubber or polyethylene terephthalate (PET) (e.g., Dacron® PET, Invista, Wichita, Kans.) cordage, covered with a biocompatible fabric or cloth to allow the ring to be sutured to the fibrous annulus tissue. More rigid cores are typically surrounded by an outer cover of both silicone and fabric as a suture-permeable anchoring margin. Annuloplasty rings may be stiff or flexible, and may have a variety of shapes in plan view, including continuous oval, circular, D-shaped, or kidney-shaped, or discontinuous C-shaped, sometimes referred to as a band. Examples are seen in U.S. Pat. Nos. 5,041,130, 5,104,407, 5,201,880, 5,258,021, 5,607,471 and, 6,187,040. Most rigid and semi-rigid annular rings for the mitral valve have a kidney-like or D shape, with a curved posterior segment co-extensive with the posterior valve leaflet, and a somewhat straighter anterior segment co-extensive with the anterior valve leaflet.

One popular annuloplasty ring is the partially flexible Carpentier-Edwards Physio® ring available from Edwards Lifesciences of Irvine, Calif. The Physio® ring is a "semi-rigid" ring because it offers selective flexibility at the posterior section while preserving the remodeling effect through a rigid anterior section. The newer Physio II® ring from Edwards Lifesciences also features up and down curves to better fit the nonplanar contours of the mitral annulus. Various other rings have posterior bows, e.g., U.S. Pat. Nos. 6,805,710 and 6,858,039, 7,959,673, or other three-dimensional configurations.

Despite numerous designs presently available or proposed in the past, there is a need for an annuloplasty ring that better accounts for the native mitral annulus anatomy.

SUMMARY

The present invention provides an annuloplasty band shaped and sized to avoid the adjacent aortic valve structure and better protects against dehiscence along the muscular mitral annulus. The band is asymmetric in that when implanted it spans more around one side of the mitral annulus than the other. In general, the band extends over the posterior leaflet and a short distance past the posterior commissure outside of the anterior leaflet. Looking down on the mitral valve with the anterior leaflet on top and the posterior leaflet at bottom, a vertical minor axis can be drawn through the midpoint of both leaflets on which is oriented a minor dimension of the mitral annulus. The annuloplasty band is discontinuous with a mid-section and two free ends, one on either side of the minor axis, and asymmetrically implants farther around the mitral annulus toward the posterior commissure than toward the anterior commissure so that the circumferential length to the right is greater than to the left. Stated another way, the asymmetric position of the implanted band is rotated in a counter-clockwise (CCW) direction around the mitral annulus from a symmetric position where the center of the band lies on the minor axis. Further, the exemplary annuloplasty band has an upward rise or bow in its mid-section that remains centered on the minor axis such that lengths of the band on either side of the high point of the rise are dissimilar. Specifically, a length extending around the mitral annulus counter-clockwise (CCW) from the high point of the rise is longer than a length extending clockwise (CW). The exemplary discontinuous mitral annuloplasty bands disclosed herein have gaps or openings between their free ends that are configured or adapted to be positioned against or adjacent the location of the aortic valve around the mitral annulus. This avoids the fibrous structure associated with the aortic valve, and better protects against dehiscence along the muscular mitral annulus.

The various asymmetrical mitral annuloplasty bands disclosed herein are adapted for implant against a mitral valve annulus. The mitral valve annulus has a posterior aspect to which a posterior leaflet attaches and an anterior aspect to which an anterior leaflet attaches. The annulus generally defines a D- or kidney-shape looking at an inflow side thereof with the anterior aspect being straighter than the more rounded posterior aspect and a minor axis intersecting and extending across the annulus between mid-points on the anterior and posterior aspects being shorter than a major axis perpendicular thereto intersecting and extending across the annulus, and wherein an anterior commissure and a posterior commissure are located on the annulus at the two junctions between the two leaflets with the anterior commissure located clockwise from the mid-point of the posterior leaflet and the posterior commissure located counter-clockwise from the mid-point of the posterior leaflet. The annulus also generally defines a saddle shape where the annulus rises up toward the left atrium at mid-points of both the anterior aspect and the posterior aspect. In various embodiments, the annuloplasty bands may be D- or kidney-shaped, oval, planar or three-dimensional.

A first embodiment of the asymmetrical mitral annuloplasty band has an elongated discontinuous body including an inner generally rigid core surrounded by a suture-permeable interface, the body defining an asymmetric shape that generally conforms to the shape of the mitral annulus and extends around the entire posterior aspect ending at a first free end located approximately at the intersection of the major axis and the annulus and extending farther around on the opposite side past the intersection of the major axis and the annulus into the anterior aspect and ending at a second free end.

A second embodiment of the asymmetrical mitral annuloplasty band has an elongated discontinuous body including an inner generally rigid core surrounded by a suture-permeable interface, the body defining an asymmetric shape commencing at a first free end adapted to be implanted adjacent the anterior commissure, a mid-section that extends in a counter-clockwise (CCW) direction around the posterior aspect past the posterior commissure into the anterior aspect and ending at a second free end.

And finally a third embodiment of the asymmetrical mitral annuloplasty band has an elongated discontinuous body including an inner generally rigid core surrounded by a suture-permeable interface, the body defining an asymmetric shape that generally conforms to the shape of the mitral annulus and extends around the entire posterior aspect and includes an upward bow corresponding with the rise in the posterior aspect, wherein the body extends clockwise along a first span from a mid-point of the upward bow to a first free and extends farther along a second span from a mid-point of the upward bow to a second free end.

In any of the first three band embodiments, a total circumferential span of the body preferably extends between about 58-67% around the mitral annulus. For example, wherein a first circumferential span of a portion of the body counterclockwise from a mid-point of the posterior aspect extends between about 37-42% around the mitral annulus, and a second circumferential span of a portion of the body clockwise from the mid-point of the posterior aspect extends between about 21-25% around the mitral annulus. Additionally, the first free end may be adapted to be implanted at the annulus on the major axis. The first free end is preferably adapted to be implanted adjacent the anterior commissure and the ring body extends in a counter-clockwise direction to the second free end within the anterior aspect.

In one of the first two band embodiments, the body may also include an upward bow centered at a mid-point of the posterior aspect. Preferably, the body has a partial saddle shape with a first high point at the upward bow, two low points located approximately at the first free end and at a location directly opposite the first free end, and a second high point at the second free end. In addition, the body may have a partial saddle shape with a first high point at the upward bow, two low points located approximately at the first free end and at a location directly opposite the first free end, and a second high point at the second free end.

In a fourth embodiment, an asymmetrical mitral annuloplasty band includes a top, a bottom, a first end, a second end, and a rigid or semi-rigid body extending between the first end and the second end, the body including a first portion and a second portion. The first portion extends counterclockwise along a path from a reference point and terminating at the first end. The second portion extends clockwise along the path from the reference point and terminating at the second end. A length of the first portion is substantially different from a length of the second portion, wherein a top view of the path has an oval, D-shape, or a kidney shape with a horizontal major axis and a vertical minor axis defining a clockface, the reference point is at 6:00, the minor axis intersects the path at 12:00 and 6:00, and the major axis intersects the path at 3:00 and 9:00 with a flatter portion of the D-shape or kidney shape above the major axis.

With regard to the fourth band embodiment, the top view of the path is preferably D-shaped, and the first portion of the body is longer than the second portion. The first portion preferably extends counterclockwise past 3:00, such as the first end being disposed at about 1:30 or even at about 1:00. In one embodiment, the second portion does not extend clockwise to 9:00, and may extend only to about 8:30, although the second portion makes it all the way to 9:00.

A fifth embodiment of an asymmetrical mitral annuloplasty band comprising a rigid or semi-rigid open band having a top and a bottom and comprising a posterior portion and an anterior portion extending from an end of the posterior portion. When viewed in plan view, the open band extends around a portion of a D- or kidney-shape having a major axis and defining a longer side having a first perimeter and a shorter side having a second perimeter shorter than the first perimeter. The major axis and D- or kidney-shape share a first intersection and a second intersection, and the D- or kidney shape has a minor axis that shares a third intersection with the longer side and a fourth intersection with the shorter side. The posterior portion of the open band extends from the first intersection along the longer side of the D- or kidney-shape, and the anterior portion of the open band extends from the first intersection along the shorter side of the D- or kidney-shape.

In the fifth embodiment of asymmetrical mitral annuloplasty band, when viewed from the top, the longer side is on the bottom and the shorter side is on the top, the first intersection is to the right and the second intersection is to the left. The posterior portion preferably does not extend to the second intersection of the D- or kidney-shape, or the posterior portion may extend to about the second intersection of the D- or kidney-shape. The anterior portion desirably does not extend to the fourth intersection.

In either of the fourth or fifth band embodiments, the asymmetrical annuloplasty band has a saddle shape with peaks at the about the intersections with the minor major axis. Preferably, the saddle shape has valleys at about the intersections with the major axis. Further, the body may have a core and a suture permeable cover disposed over the core. The core may comprise at least one of cobalt-chromium alloy, titanium alloy, stainless steel, or, and may be a solid core, a plurality of bands, or a braided core. The suture permeable cover preferably includes an elastomeric sleeve disposed around the core and a fabric outer cover disposed over the elastomeric sleeve. The suture permeable cover also may have a radially outwardly projecting sewing flange.

Another aspect of the present application is a set of progressively saddled asymmetrical mitral annuloplasty bands comprising a plurality of sizes of any of the asymmetrical mitral annuloplasty bands described above, wherein a ratio of height of the saddle to size of the asymmetrical mitral annuloplasty band is not constant. For example, the ratio of height to size increases with size, or the ratio of height to size varies continuously with size. At a minimum, the ratio of height to size varies in at least one step with size. Also, a ratio of length of the minor axis to size in the set of bands may not be constant. For instance, the ratio of length of the minor axis to size increases with size and may vary continuously with size. At a minimum, the ratio varies in at least one step with size.

Other aspects of the present application are methods of repairing a mitral valve in need thereof, the mitral valve comprising an anterior leaflet including regions A1, A2, and A3; a posterior leaflet including regions P1, P2, and P3; an antero-medial commissure; a postero-lateral commissure; and two trigones.

A first method includes securing a mitral band to an annulus of a mitral valve with a first end thereof proximate to the anterior leaflet, a body thereof extending around one of the antero-medial commissure or the postero-lateral commissure; and a second end thereof proximate to the posterior leaflet, or the other of the antero-medial commissure or the postero-lateral commissure.

A second method of repairing a mitral valve in need comprises securing a mitral band comprising a first end and a second end to an annulus of a mitral valve with the first end proximate to the anterior leaflet and the second end not proximate to the anterior leaflet.

And finally a third method of repairing a mitral valve includes securing a mitral band comprising a first end and a second end to an annulus of a mitral valve with the first end proximate to the anterior leaflet, wherein the mitral band is asymmetric relative to a plane passing through A2 and P2.

In the methods described above, securing the mitral band preferably comprises securing the first end proximate to A3; and the second end proximate to P1 or the antero-medial commissure. Also, securing the mitral band desirably comprises securing the mitral band to follow the natural saddle shape of the annulus of the mitral valve.

A further understanding of the nature and advantages of the invention will become apparent by reference to the remaining portions of the specification and drawings.

BRIEF DESCRIPTION OF THE DRAWINGS

Features and advantages of the present invention will become appreciated as the same become better understood with reference to the specification, claims, and appended drawings wherein:

FIGS. 3A-3D are elevational and plan views of an exemplary annuloplasty band of the present invention;

FIGS. 4A and 4B are sectional views of the exemplary annuloplasty band taken along corresponding sections lines in FIG. 3B;

DETAILED DESCRIPTION OF CERTAIN EMBODIMENTS

The present application discloses an asymmetric mitral annuloplasty band that avoids the adjacent aortic valve structure and better protects against dehiscence along the muscular mitral annulus. The term "band" is used here since the implant is a discontinuous ring, although in some contexts such implants are also termed "rings". Indeed, the bands disclosed herein define shapes that circumscribe a majority of the mitral annulus, and thus trace most of a ring shape. A complete ring shape may be constructed, and indeed the shape of the bands may be defined, by imagining an extension of the shape between and connecting the free ends. For example, the preferred plan view shape of the disclosed bands is kidney or D-shaped so as to conform to the peripheral shape of the usual mitral annulus. Therefore "band" and "ring" are synonymous, the disclosed band or ring simply being discontinuous so as to have two free ends.

The term "axis" in reference to the illustrated annuloplasty bands, and other non-circular or non-planar bands, refers to a line generally through the centroid of the band or ring periphery when viewed in plan view. "Axial" or the direction of the "axis" can also be viewed as being parallel to the average direction of blood flow within the valve orifice and thus within the band when implanted therein. Stated another way, an implanted mitral band or ring orients about a central flow axis aligned along an average direction of blood flow through the mitral annulus from the left atrium to the left ventricle.

Figure 1:
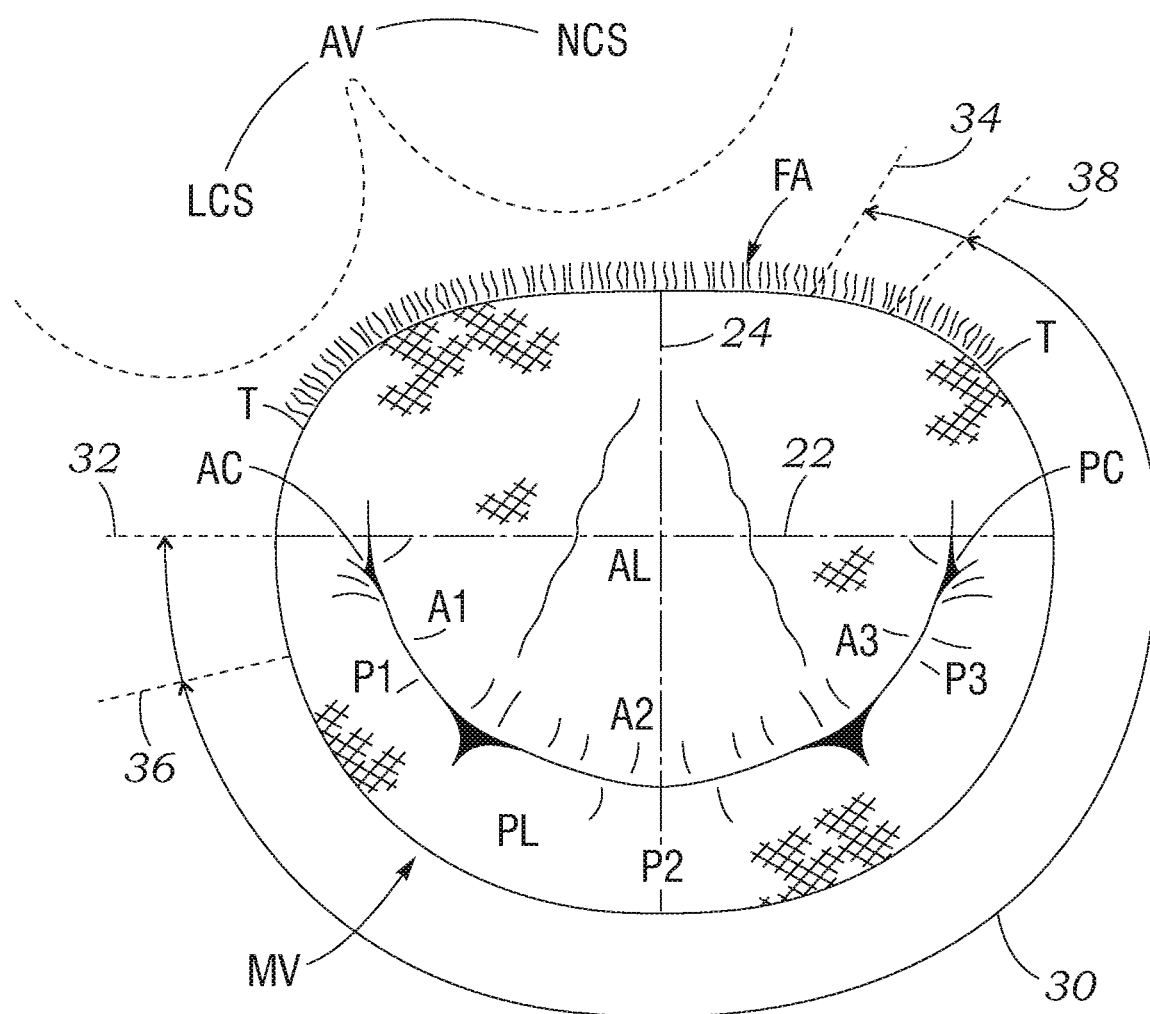
FIG. 1 is a superior or plan view of a healthy mitral valve, with the leaflets closed and coapting at peak contraction pressures during ventricular systole and indicating the primary anatomical landmarks as well as diagram lines indicating the circumferential reach of bands of the present application.

FIG. 1 is a plan view of the mitral valve with posterior being down and anterior being up. In a healthy heart, the annulus of the mitral valve MV creates an anatomic shape and tension such that a posterior leaflet PL and an anterior leaflet AL coapt in the flow orifice, forming a tight junction, at peak contraction or systolic pressures, as seen in FIG. 1. The mitral valve MV annulus has a posterior aspect to which the posterior leaflet PL attaches and an anterior aspect to which the anterior leaflet AL attaches. Where the leaflets meet at the opposing medial and lateral sides of the annulus are called the leaflet commissures: the anterior (or more accurately, the antero-medial) commissure AC, and the posterior (or postero-lateral) commissure PC. The posterior leaflet is divided into three scallops or cusps, sometimes identified as P1, P2, and P3, starting from the anterior commissure and continuing in a counterclockwise direction to the posterior commissure. The posterior scallops P1, P2, and P3 circumscribe particular arcs around the periphery of the posterior aspect of the annulus, which may vary depending on a variety of factors, including actual measurement of the mitral valve posterior leaflet scallops, and surgeon preference. As a rule, however, a major axis 22 of the mitral annulus intersects both the first and third posterior scallops P1 and P3, approximately at the commissures AC, PC, and a minor axis 24 intersects and generally bisects the middle posterior scallop P2. The anterior leaflet also features scallops or regions labeled A1, A2, and A3 as indicated in FIG. 1.

The mitral anterior leaflet AL attaches to the fibrous portion FA of the mitral annulus, which makes up about one-third of the total mitral annulus circumference. The muscular portion of the mitral annulus constitutes the remainder of the mitral annulus, and the posterior leaflet PL attaches thereto. The anterior fibrous annulus FA, the two ends of which are called the fibrous trigones T, forms part of the central fibrous body of the heart. The anterior commissure AC and the posterior commissure PC are located just posterior to each fibrous trigone.

The fibrous mitral valve annulus FA is intimate with or adjacent to the aortic valve AV, in particular the left coronary sinus LCS and non-coronary sinus NCS. The central fibrous body is fairly resistant to elongation, and thus the great majority of mitral annulus dilation occurs in the posterior two-thirds of the annulus, or around the muscular mitral annulus.

In a preferred embodiment, the mitral annuloplasty bands disclosed herein comprise discontinuous rings defining a kidney or D-shape with a substantially complete posterior segment centered about a minor axis of the band. Further, the annuloplasty band defines two anterior segments with free ends opposite each other and having differing lengths extending from the posterior segment. The different lengths of the two anterior segments of the band create an asymmetry which is imbalanced toward the posterior commissure.

To better define the contours of the asymmetric annuloplasty band disclosed herein, FIG. 1 illustrates a circumferential span 30 around the mitral annulus, generally illustrating the range of lengths of the band. More particularly, the longest length of band extends around in a counter-clockwise (CCW) direction between a radial angular location 32 at the anterior commissure AC to a radial angular location 34 that is within the fibrous mitral annulus and above the posterior commissure PC. It will be understood that the asymmetric band extends around the mitral annulus in a span that avoids the adjacent aortic valve structures of the left coronary sinus LCS and non-coronary sinus NCS. The aortic valve AV is believed to be located slightly offset from the minor axis 24 as shown. In addition, the portion of the right side of the band that extends around to the posterior commissure PC provides reinforcement and reduces dehiscence, or suture pull-out, in that area. In general, the band extends circumferentially around the posterior leaflet PL and a short distance past the posterior commissure PC around the anterior leaflet AL.

To help better define this span, clock positions may be assigned relative to the major axis 22 and minor axis 24 of the mitral valve MV; that is, the vertical minor axis 24 extends between and defines 12:00 and 6:00, and the horizontal major axis 22 extends between and defines 3:00 and 9:00. Using this nomenclature, the longest band illustrated in FIG. 1 extends between radial location 32 at about 9:00 and radial location 34 at about 1:00. Of course, these geometries may be expressed in percent of a continuous ring or in degrees, and the aforementioned largest span 30 therefore is about 67% around the mitral annulus or about 240°.

The radial locations 32, 34 correspond to the free ends of the band. Each free end may be independently shortened as indicated to secondary radial locations 36 and 38. Radial location 36 is at about 8:30 and radial location 38 is at about 1:30. Consequently, the shortest band may span about 58% around the mitral annulus or about 210°. Intermediate bands where one end is shortened but not the other are also contemplated, corresponding to bands spanning about 62% around the mitral annulus or 225°.

Figure 2:
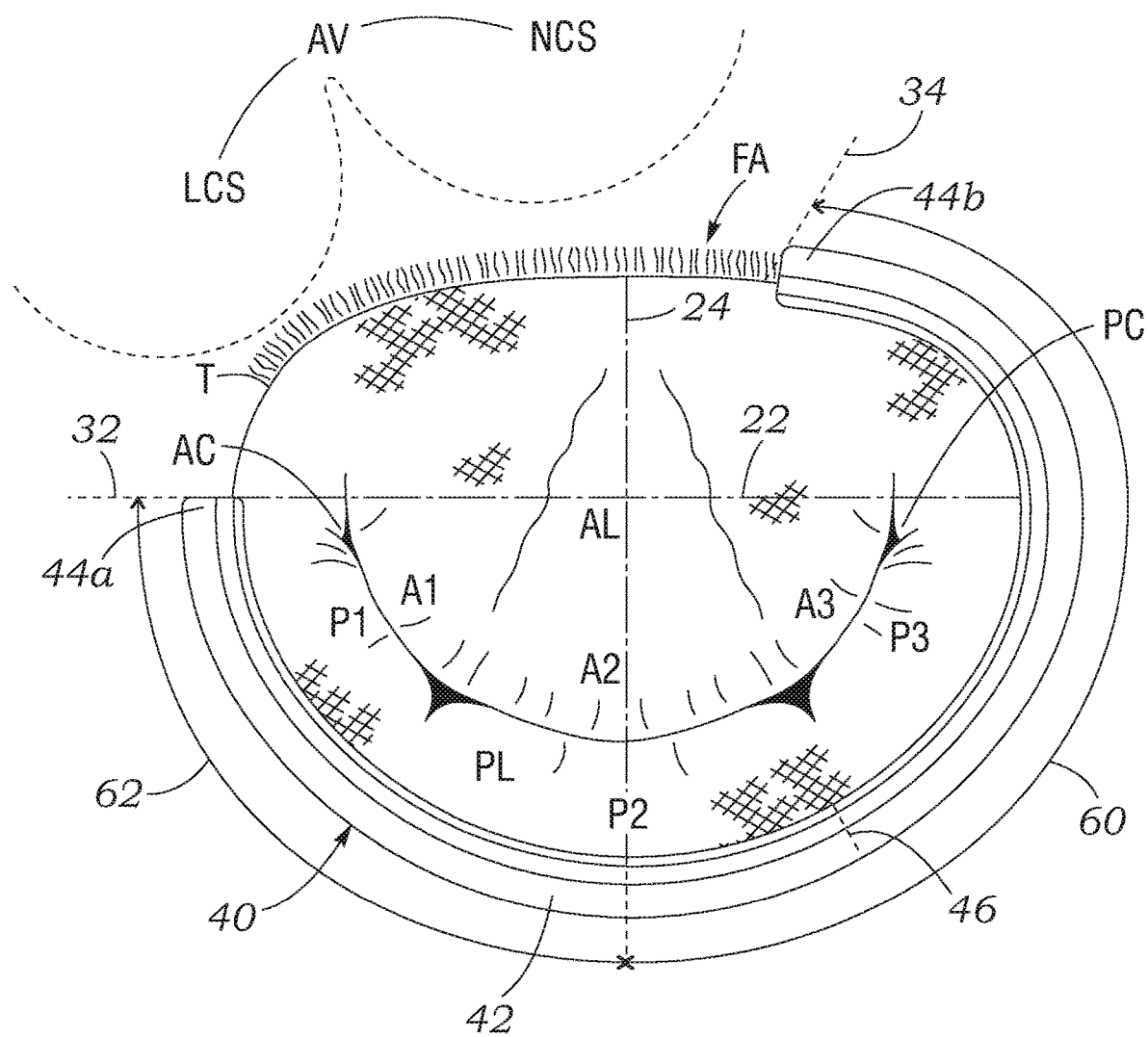
FIG. 2 is a plan view of a mitral valve as in FIG. 1 with an exemplary annuloplasty band of the present application shown implanted therearound.

FIG. 2 illustrates the mitral valve and anatomical landmarks with an exemplary annuloplasty band 40 secured thereto. The band 40 is shaped and sized to avoid the adjacent aortic valve AV structure and better protects against dehiscence along the muscular mitral annulus. The band 40 is asymmetric when implanted in that it extends farther around one side of the mitral annulus than around the other. That is, it is asymmetric relative to the minor axis 24 of the annulus. Looking down on the mitral valve as in FIG. 2, the vertical minor axis 24 extends through the midpoint of both leaflets AL, PL. The annuloplasty band 40 is discontinuous with a mid-section 42 and two free ends 44a, 44b, one on either side of the minor axis 24. The band 40 asymmetrically extends farther CCW around the mitral annulus toward the posterior commissure PC than CW toward the anterior commissure AC so that its circumferential length to the right is larger or longer than to the left. Stated another way, the asymmetric position of the implanted band 40 is rotated in a counter-clockwise (CCW) direction around the mitral annulus from a symmetric position so that the circumferential center of the band (located at about number 46) lies CCW from the minor axis 24.

As seen in FIGS. 3A-3D, the exemplary annuloplasty band 40 has a gentle upward rise or bow 50 along a vertical axis 48 in its mid-section 42 that remains centered on the minor axis 24. (The vertical axis 48 is perpendicular to both the major axis 22 and minor axis 24 and extends through their intersection.) The bow 50 diminishes on either side of the minor axis 24 to low points around the ring at about the major axis 22. Since the first free end 44a lies on or adjacent the major axis 22 it also generally corresponds to a first one of the low points. A second low point 52 occurs in the band mid-section 42 along the major axis 22 opposite to the first free end 44a. The band 40 then rises up from the second low point 52 toward the second free end 44b. If the band 40 were continuous, as indicated by the dashed line extension 54 in FIG. 3C, it would define a saddle shape with both the anterior and posterior sections bowed upward (convex up) with the sides that cross the major axis 22 being curved downward (convex down). Of course, this discussion refers to a relative orientation in which "up" corresponds to the left atrium and "down" to the left ventricle, so that blood flows downward through the annulus.

As seen in FIGS. 2, 3A, and the bottom view of FIG. 3C, the upward bow 50 of the annuloplasty band 40 is centered on the minor axis 24 such that lengths of the band on either side of the high point of the bow are dissimilar. Specifically, a first span 60 that extends counter-clockwise (CCW) from the high point of the bow 50 at the minor axis 24 is longer than a second span 62 that extends clockwise (CW) (directions are reversed in the bottom view of FIG. 3C). As explained above, the spans of the band 40 on either side of the minor axis 24 differ, with the first span 60 extending past the posterior commissure PC of the mitral annulus and the second span 62 extending approximately to or just short of the anterior commissure AC. Using the aforementioned expressions, the first span 60 extends CCW from the minor axis 24 to a farthest extent of about 1:00 or about 42% (150°) around the mitral annulus, while the second span 62 extends CW from the minor axis 24 to a farthest extent of about 9:00 or about 25% (90°) around the mitral annulus. Further, the first and second spans 60, 62 may independently be somewhat shorter, as indicated by the radial lines 36 and 38 in FIG. 1.

FIGS. 4A and 4B are sections views of the annuloplasty band 40 taken along corresponding sections lines in FIG. 3B. In a preferred embodiment, the band construction includes a relatively rigid or semi-rigid inner core 70 surrounded by a suture-permeable interface that may include an elastomeric sleeve 72 closely surrounding the core and a fabric outer cover 74, for example, a polyethylene terephthalate (PET) fabric cover. In the preferred embodiment the elastomeric sleeve 72, which may be silicone rubber, is molded to have an outwardly-extending flange 76 to facilitate suturing of the band 40 to the mitral annulus. The band 40 may be secured with sutures, staples, or other such devices to an inside ledge of the mitral annulus. In a typical procedure, an array of sutures are anchored through the annulus and then threaded through corresponding locations around the band 40, and then the band is parachuted down the suture array to be seated at the annulus before tying off the sutures.

Figure 5C:
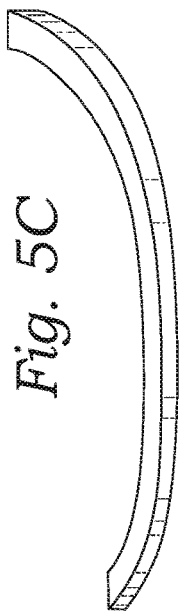
FIGS. 5A-5C are elevational and plan views of an exemplary inner core for the annuloplasty band of FIGS. 3A-3D.
Figure 5A:
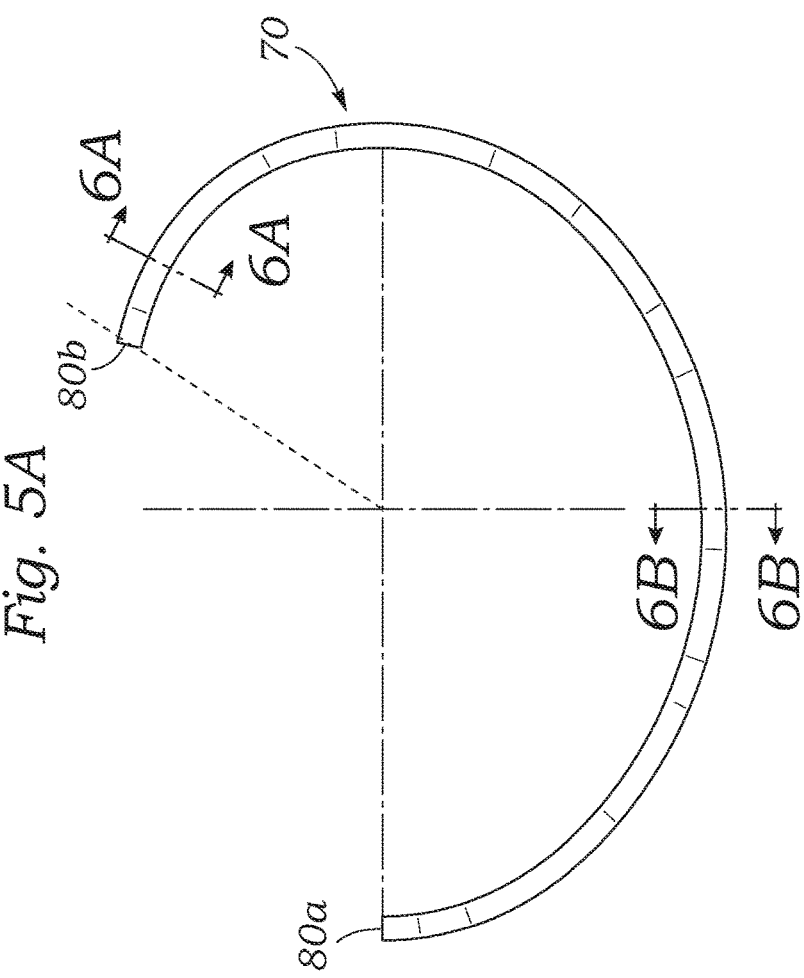
Figure 5B:
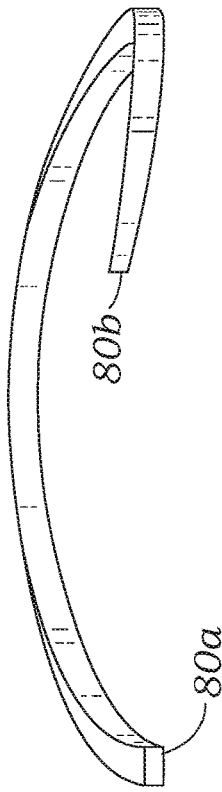

FIGS. 5A-5C show an exemplary inner core 70 for the annuloplasty band 40. The core 70 may comprises a variety of materials and cross-sections, and is shown rectangular in the illustrated embodiment. As indicated by the sections 4A/6A and 4B/6B taken through different locations of the band 40 and core 70, the core is desirably thicker in a mid-section than towards free ends 80a, 80b thereof. This provides some flexibility near the free ends 44a, 44b of the band 40 to help avoid dehiscence, or suture pull-out.

The annuloplasty bands of the present invention are "generally rigid" in that they will resist distortion when subjected to the stress imparted thereon by the mitral valve annulus of an operating human heart. In this sense, "distortion" means substantial permanent deformation from a predetermined or manufactured shape. A number of "generally rigid" materials can be utilized as an inner core of the bands that will perform this function, including various biocompatible polymers, metals, alloys, and combinations or composites thereof. For example, certain polyesters that resist distortion and also rapid degradation within the body may be used (a material that degrades slowly may provide the required initial support). In a preferred embodiment, at least an inner core or body of the annuloplasty band of the present invention is made of a suitable metal, such as cobalt-chromium (Co—Cr) alloys (for example, ELGILOY® Co—Cr made by Elgiloy, L.P. of Elgin, Ill., U.S.A), also titanium or its alloys (for example, titanium-6-4, which contains about 6% aluminum and 4% vanadium by weight), stainless steel, nitinol, or combinations thereof.

Figure 6A:
FIGS. 6A and 6B are sections views of the inner core taken along corresponding sections lines in FIG. 5A.
Figure 6B:
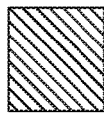

The core or band body may be one piece, or may include a plurality of concentric bands held together or otherwise cooperating elements, or any combination thereof. Embodiments of one-piece cores include a square/rectangular cross section, for example, as illustrated in FIGS. 6A and 6B, or a core having another shape, for example, a convex polygon, a circle, or an oval. Other embodiments of the core include at least one channel, for example, a C-shape or an H-shape cross section. As shown in FIGS. 6A and 6B, the cross-sectional shape can vary along the length of the core. As such, some cores include at least one portion that includes a channel, for example, along the mid-section, and another portion without a channel, for example, at one or both ends.

Embodiments in which the core comprises bands include cores in which the bands are stacked radially or concentrically, and/or axially. The flexibility or rigidity of one or more selected portions of such cores can be adjusted, for example, by varying the number of bands at the portion, changing a thickness of at least one band in the portion, incorporating at least one band comprising a different material, or any combination thereof. Some embodiments include a spacer between at least one adjacent pair of bands, for example, a polymer and/or elastomer spacer. Other embodiments of multi-piece cores include braided cores, which are braided from a plurality of wires, strands, and/or braids.

The annuloplasty bands of the present invention are also especially suited to correcting particular pathologies. That is, the present invention contemplates a set of bands defined by band bodies wherein the proportional shapes of the band bodies change with increasing nominal orifice sizes of the band bodies in the set. The orifice size generally refers to the nominal length across the major axis of the band body, although some rings or bands deviate from this nomenclature. Typically, annuloplasty rings and bands have orifice sizes in even millimeter increments (e.g., 24 mm, 26 mm, etc., up to about 40 mm) as measured across the major axes. Other sizing schemes are also possible, for example, odd millimeter increments, every millimeter increments, or combination schemes, for example, every millimeter up to a certain size, then even increments above that size. Such rings will have distinct packaging so as to be labeled with the particular size. The change of band shape depends on the pathology being corrected. For instance, pathologies resulting in mitral regurgitation may benefit from a set of bands which have increasing circularity as the band size increases. It is important to understand that the set of bands is formed of band bodies that are formed during manufacture to be "generally rigid" and not easily manipulated. One example is a band core formed of bands of Elgiloy® Co—Cr alloy. It should also be mentioned that holders for such annuloplasty bands have peripheral shapes that conform to the optimally-sized bands.

Some sets of the annuloplasty band include progressively sized bands, that is, at least one dimension that does not scale linearly with the labeled size of the band. Because the labeled size is related to the major axis length, as described above, the progressivity or nonlinearity is described with respect to the major axis length, unless otherwise specified. Examples of dimensions that are progressively sized in embodiments of sets include the length of the minor axis, and the height or degree of saddle. Another variable subject to progressivity is flexibility of at least one portion of the band. Some sets include bands with combinations of progressive dimensioning, for example, minor axis length and saddle height.

In some sets, every band in the set is progressively sized along at least one dimension. In some sets, the progressive sizing is applied in steps, for example, to sub-sets or ranges of band sizes rather than on every individual band. For example, some sets include a first range of band sizes in which a dimension scales proportionally with size, and a second range of band sizes in which the same dimension also scales proportionally with size, but where the proportion is different between the first range and the second range. In some sets, a first range of sizes is not progressively sized, for example, smaller bands, and a second range is progressively sized, for example, larger bands.

As discussed above, in some sets, a ratio between the minor axis 24 and major axis 22 changes with size. In some embodiments, this aspect ratio increases with labeled size. For example, some bands described herein can be defined as a part of a D-shape, as shown in the drawings, but bands for sizes of about 36 mm and up are more rounded. Consequently, in some embodiments, at larger sizes, the band curves become more symmetric in plan view across the major axis 22 (see FIG. 2), at least on the longer side.

In another example, a set of bands has increasing saddle profiles for larger sizes, though not linearly increasing. That is, a preferred set of bands has a relatively flat saddle (smaller upward bows) for bands under about 30 mm, a constant moderate saddle shape in bands of from about 24-30 mm, while the larger bands from about 36-40 mm have more pronounced saddles.

In another set of bands, the saddle increases proportionately with size at smaller sizes, and progressively at larger sizes. A variation includes a middle range in which the saddle increases progressively, but less aggressively than for the larger sizes.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. An asymmetrical mitral annuloplasty band adapted for implant against a mitral valve annulus, the mitral valve annulus having a posterior aspect to which a posterior leaflet attaches and an anterior aspect to which an anterior leaflet attaches, the annulus generally defining a D- or kidney-shape looking at an inflow side thereof with the anterior aspect being straighter than the more rounded posterior aspect and a minor axis intersecting and extending across the annulus between mid-points on the anterior and posterior aspects being shorter than a major axis perpendicular thereto intersecting and extending across the annulus, and wherein an anterior commissure and a posterior commissure are located on the annulus at the two junctions between the two leaflets with the anterior commissure located clockwise from the mid-point of the posterior leaflet and the posterior commissure located counter-clockwise from the mid-point of the posterior leaflet, the band comprising:
an elongated discontinuous body including an inner rigid or semi-rigid core surrounded by a suture-permeable interface, the body defining an asymmetric shape as viewed in top plan view that generally conforms to a portion of the shape of the mitral annulus and extends around the entire posterior aspect ending at a first free end and extending counterclockwise farther around on an opposite side past the intersection of the major axis and the annulus into the anterior aspect and ending at a second free end, the body defining a gap between the first and second free ends, wherein the body has a partial saddle shape with a first high point at an upward bow centered at a mid-point of the posterior aspect, two low points located approximately at intersections of the major axis and the annulus when the ring is implanted, and a second high point at the second free end.

2. The mitral annuloplasty band of claim 1, wherein a total circumferential span of the body extends between 58-67% around the mitral annulus, and a first circumferential span of a portion of the body counterclockwise from a mid-point of the posterior aspect extends between 37-42% around the mitral annulus.

3. The mitral annuloplasty band of claim 1, wherein the first free end is adapted to be implanted adjacent the anterior commissure and the body extends in a counter-clockwise direction to the second free end within the anterior aspect.

4. The mitral annuloplasty band of claim 1, wherein the inner rigid or semi-rigid core is rectangular and is thicker in a mid-section than closer to the first and second free ends.

5. The mitral annuloplasty band of claim 4, wherein the inner rigid or semi-rigid core is made of a metal selected from the group consisting of cobalt-chromium (Co—Cr) alloy, titanium, titanium alloy, stainless steel, nitinol, and combinations thereof.

6. An asymmetrical mitral annuloplasty band adapted for implant against a mitral valve annulus, the mitral valve annulus having a posterior aspect to which a posterior leaflet attaches and an anterior aspect to which an anterior leaflet attaches, the annulus generally defining a D- or kidney-shape looking at an inflow side and a saddle shape where the annulus rises up toward the left atrium at mid-points of both the anterior aspect and the posterior aspect, the band comprising:
an elongated discontinuous body including an inner rigid or semi-rigid core surrounded by a suture-permeable interface, the body defining an asymmetric shape as viewed in top plan view that generally conforms to a portion of the shape of the mitral annulus and extends around the entire posterior aspect when the ring is implanted and includes an upward bow corresponding with the rise in the posterior aspect, wherein the body extends clockwise along a first span from a mid-point of the upward bow to a first free end and extends farther along a second span from a mid-point of the upward bow to a second free end, the body defining a gap between the first and second free ends, wherein the body has a partial saddle shape with a first high point at the upward bow, two low points located approximately at an intersections of the major axis and the annulus when the ring is implanted, and a second high point at the second free end.

7. The mitral annuloplasty band of claim 6, wherein the band has a relatively flat partial saddle shape if the major axis is under about 30 mm, and a more pronounced partial saddle shape if the major axis is between 36-40 mm.

8. The mitral annuloplasty band of claim 6, wherein a total circumferential span of the body extends between 58-67% around the mitral annulus, and the second span extends between 37-42% around the mitral annulus.

9. The mitral annuloplasty band of claim 6, wherein the first free end is adapted to be implanted at the annulus on the major axis.

10. The mitral annuloplasty band of claim 6, wherein the inner rigid or semi-rigid core is rectangular and is thicker in a mid-section than closer to the first and second free ends.

11. The mitral annuloplasty band of claim 10, wherein the inner rigid or semi-rigid core is made of a metal selected from the group consisting of cobalt-chromium (Co—Cr) alloy, titanium, titanium alloy, stainless steel, nitinol, and combinations thereof.

12. An asymmetrical mitral annuloplasty band the mitral valve annulus having a posterior aspect to which a posterior leaflet attaches and an anterior aspect to which an anterior leaflet attaches, the annulus generally defining a D- or kidney-shape looking at an inflow side and a saddle shape where the annulus rises up toward the left atrium at mid-points of both the anterior aspect and the posterior aspect, the band comprising:

a top, a bottom, a first end, a second end, and a rigid or semi-rigid discontinuous body extending between the first end and the second end, the body including a first portion and a second portion, the body surrounded by a suture-permeable interface and generally conforming to a portion of the shape of the mitral annulus;

the first portion extending clockwise along the path from the reference point and terminating at the first end; and the second portion extending counterclockwise along a path from a reference point and terminating at the second end;

a length of the second portion is longer than a length of the first portion, wherein a top plan view of the path has a discontinuous D-shape, or a kidney shape with a gap between the first and second ends and a horizontal major axis and a vertical minor axis perpendicular to the major axis at a central axis that is perpendicular to both major and minor axes, wherein the reference point is on the minor axis below the central axis, the minor axis intersects the path at the reference point below the central axis, and the major axis intersects the path at locations to the left and right of the central axis, with a flatter portion of the D-shape or kidney shape above the major axis, and wherein the asymmetrical annuloplasty band has a saddle shape with diametrically opposed valleys at the intersections with the major axis.

13. The asymmetrical mitral annuloplasty band of claim 12, wherein the top view of the path is D-shaped.

14. The asymmetrical mitral annuloplasty band of claim 12, wherein the second portion extends counterclockwise past the intersection of the major axis with the path, and is disposed past the intersection of the major axis with the path by about 45° counter-clockwise.

15. The asymmetrical mitral annuloplasty band of claim 14, wherein the second end is located past the intersection of the major axis with the path by about 60° counter-clockwise.

16. The asymmetrical mitral annuloplasty band of claim 12, wherein the first portion extends clockwise along the path less than 90° from the reference point.

17. The asymmetrical mitral annuloplasty band of claim 12, wherein the first portion extends clockwise along the path about 90° clockwise from the reference point.

18. The asymmetrical mitral annuloplasty band of claim 12, wherein the band has a relatively flat saddle shape if the major axis is under 30 mm, and a more pronounced saddle shape if the major axis is between 36-40 mm.

19. The mitral annuloplasty band of claim 12, wherein the inner rigid or semi-rigid core is rectangular and is thicker in a mid-section than closer to the first and second ends.

20. The mitral annuloplasty band of claim 19, wherein the inner rigid or semi-rigid core is made of a metal selected from the group consisting of cobalt-chromium (Co—Cr) alloy, titanium, titanium alloy, stainless steel, nitinol, and combinations thereof.

* * * * *